United States Patent
Chougrani et al.

(10) Patent No.: US 10,081,572 B2
(45) Date of Patent: Sep. 25, 2018

(54) COPOLYMERS HAVING GEM-BISPHOSPHONATE GROUPINGS

(75) Inventors: Kamel Chougrani, Loury (FR); Frederic Leising, Avilly Saint Leonard (FR)

(73) Assignee: CHRYSO, Issy les Moulineaux (FR)

( * ) Notice: Subject to any disclaimer, the term of this patent is extended or adjusted under 35 U.S.C. 154(b) by 0 days.

(21) Appl. No.: 14/111,752

(22) PCT Filed: Apr. 13, 2012

(86) PCT No.: PCT/EP2012/056840
§ 371 (c)(1),
(2), (4) Date: Oct. 16, 2013

(87) PCT Pub. No.: WO2012/140235
PCT Pub. Date: Oct. 18, 2012

(65) Prior Publication Data
US 2014/0039098 A1    Feb. 6, 2014

(30) Foreign Application Priority Data
Apr. 15, 2011 (FR) ...................... 11 53312

(51) Int. Cl.
| | | |
|---|---|---|
| C08F 8/40 | (2006.01) | |
| C04B 16/04 | (2006.01) | |
| C04B 24/24 | (2006.01) | |
| C04B 24/26 | (2006.01) | |
| C08F 220/26 | (2006.01) | |
| C04B 28/02 | (2006.01) | |
| C08F 22/10 | (2006.01) | |
| C08L 33/08 | (2006.01) | |
| C07F 9/38 | (2006.01) | |
| C08F 230/02 | (2006.01) | |
| C08F 220/28 | (2006.01) | |
| C04B 103/32 | (2006.01) | |
| C04B 111/20 | (2006.01) | |

(52) U.S. Cl.
CPC ............ *C04B 16/04* (2013.01); *C04B 24/243* (2013.01); *C04B 24/2647* (2013.01); *C04B 28/02* (2013.01); *C07F 9/386* (2013.01); *C07F 9/3873* (2013.01); *C08F 8/40* (2013.01); *C08F 22/10* (2013.01); *C08F 220/26* (2013.01); *C08L 33/08* (2013.01); *C04B 2103/32* (2013.01); *C04B 2111/20* (2013.01); *C04B 2111/2015* (2013.01); *C08F 230/02* (2013.01); *C08F 2220/286* (2013.01)

(58) Field of Classification Search
None
See application file for complete search history.

(56) References Cited

U.S. PATENT DOCUMENTS

| | | | | |
|---|---|---|---|---|
| 4,207,405 | A * | 6/1980 | Masler et al. ............. | 525/327.4 |
| 4,877,603 | A * | 10/1989 | Degenhardt et al. ........... | 424/57 |
| 4,963,347 | A * | 10/1990 | Humphries et al. ........... | 424/49 |
| 5,490,978 | A * | 2/1996 | Spaltro et al. .................. | 424/49 |
| 2007/0043190 | A1* | 2/2007 | Kraus ................. | C04B 24/2647 |
| | | | | 526/319 |
| 2008/0146700 | A1* | 6/2008 | Kraus ................... | C08F 212/14 |
| | | | | 524/3 |

FOREIGN PATENT DOCUMENTS

| | | |
|---|---|---|
| CN | 101128495 A | 2/2008 |
| CN | 101333092 A | 12/2008 |
| CN | 101370747 A | 2/2009 |
| CN | 101659530 A | 3/2010 |
| EP | 2697274 A1 | 2/2014 |
| FR | 2776285 A1 | 9/1999 |
| FR | 2 892 420 A1 | 4/2007 |
| JP | 2759688 | 3/1998 |
| JP | 2 759688 B2 | 5/1998 |
| JP | 2010512371 A | 4/2010 |
| KR | 10-2008-0065686 A | 7/2008 |
| WO | WO 2007/053563 A2 | 5/2007 |

* cited by examiner

*Primary Examiner* — Robert C Boyle
(74) *Attorney, Agent, or Firm* — Knobbe, Martens, Olson & Bear, LLP

(57) ABSTRACT

A copolymer includes a main hydrocarbon chain and side groups including carboxylic groups and polyoxyalkylate groups. The copolymer further includes gem-bisphosphonate groups. A composition, such as n admixture for suspensions of mineral particles, includes the copolymer. The copolymer can be used for fluidifying suspensions of mineral particles and maintaining the fluidity of such suspensions. The copolymer can also be used for reducing the sensitivity of hydraulic compositions to clays and alkaline sulfates.

14 Claims, No Drawings

COPOLYMERS HAVING GEM-BISPHOSPHONATE GROUPINGS

The present invention relates to copolymers with gem-biphosphonate groups, to a method for their preparation and to their use as fluidifiers of suspensions of mineral particles, notably compositions of cements and plaster formulations.

STATE OF THE ART

Generally, admixtures are added to cement compositions for improving their properties. Rheological properties and their change over time, related to their workability, are among the fundamental properties of cement compositions.

Fluidifiers or plasticizers are in particular used, which have the effect of fluidifying cement compositions and thus allow a reduction in the amount of water added, this is why they are also designated as water reducing agents. The composition then has a higher density and results in a material having a higher mechanical strength.

Certain soluble polymers called superplasticizers give the possibility of further reducing the amount of water. Superplasticizers of the type of polyalkoxylated polycarboxylic acids (PCPs) are notably known.

Document FR 2892420 describes superplasticizers with phosphonate and polyoxyalkylate groups for fluidifying suspensions of mineral particles, in which the phosphonate groups are amino-bisalkylenephosphonic groups of the following formula (A):

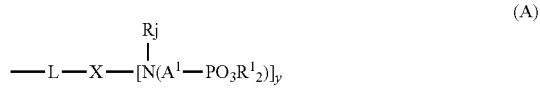
(A)

wherein L represents a group for binding to the main chain and X is an alkylene or oxyalkylene group. Phosphonate monomers may notably be obtained by diphosphonation according to the conditions of the MOEDRITZER-IRANI reaction by reaction of an amine with formaldehyde and phosphorous acid.

In order to access these structures, chemical modification of a polymer by post-grafting is also proposed. This method includes two steps, i.e. the copolymerization of an unsaturated carboxylic acid with a polyethoxylated (meth)acrylic ester followed by grafting of a phosphonate amine or alcohol synthon or, alternatively, polymerization of the unsaturated carboxylic acid and subsequent esterification with polyalkoxylate compounds followed by grafting of a phosphonate synthon.

Technical Problem

The object of the invention is to provide novel modified copolymers useful as admixtures for suspensions of mineral particles.

Another object is to provide a method for preparing these copolymers which is simple and economical and in particular does not require the use of formaldehyde.

Still another object is to provide admixtures for suspensions of mineral particles having substantial water reducing power, good maintenance of rheology, low sensitivity to alkaline sulfates and to clays and good robustness towards different cements.

SUMMARY OF THE INVENTION

The objects mentioned above are achieved according to the invention with copolymers including gem-biphosphonic groups.

Thus, according to the invention a copolymer is provided, comprising a main hydrocarbon chain and side groups, wherein the side groups comprise carboxylic groups, polyoxyalkylate groups and gem-biphosphonate groups.

According to a second aspect, the invention is directed to a method for preparing these copolymers comprising the steps:
(i) polymerizing a monomer bearing a carboxylic group, optionally in the presence of a monomer bearing a polyoxyalkylate group; and
(ii) grafting the obtained polymer with a reactive gem-biphosphonate compound.

The gem-bisphosphonate copolymer thereby obtained is advantageously formulated before use, preferably as a solution, notably as an aqueous solution. The formulation may also include the customary additives in this field.

According to another aspect, the invention is therefore directed to an admixture for suspensions of mineral particles comprising the copolymer according to the invention as a solution in a suitable solvent or in a dry form, notably as a powder.

Moreover, the invention according to another aspect is directed to the use of the copolymer according to the invention for fluidifying suspensions of mineral particles and/or for maintaining the workability of hydraulic binders. It is also directed to the use of the copolymer according to the invention for reducing the sensitivity of hydraulic compositions to clays and alkaline sulfates.

Finally, according to a last aspect, the invention is directed to a composition of mineral particles comprising the copolymer according to the invention.

Definitions

Within the scope of the present discussion, by the term of «suspension of mineral particles» or «hydraulic composition» is meant any binder with hydraulic setting, i.e. notably in addition to cements such as Portland cements, aluminous cements, mortars further comprising fine granulates, concretes further comprising coarse granulates or further anhydrous calcium sulfate or semi-hydrates thereof. The term also encompasses inert mineral fillers such as calcium sulfate dihydrates as well as calcium carbonate, silica, titanium hydroxide and clay compounds.

By the term of «hydrocarbon chain» is meant an aliphatic, saturated or unsaturated, aromatic, arylalkyl or alkylaryl, linear or branched group, including carbon and hydrogen atoms, optionally interrupted and/or terminated with one or several hetero-atoms such as S, O, N, P.

The term of «gem-bisphosphonate group» is meant to refer to groups including two phosphonate groups bound to a same carbon atom. These groups therefore have a P—C—P bond.

By the term of «alkyl group» is meant a linear, branched or cyclic alkyl group.

In the same way, by the term of «alkylene group» is meant a linear or cyclic alkylene group.

DETAILED DESCRIPTION OF THE INVENTION

The copolymers according to the invention are comb copolymers including a main hydrocarbon chain on the one hand and side groups on the other hand. They are further characterized by the presence of carboxylic groups, polyoxyalkyl groups and gem-bisphosphonate groups as side groups.

The simultaneous presence of these three types of groups gives the copolymer interesting properties as an admixture, notably of a superplasticizer, for suspensions of mineral particles.

[Copolymers]

In their widest definition, the copolymers proposed according to the invention are modified polymers of the PCP type including gem-bisphosphonate groups.

The polymer is of the comb type, including a main chain and side groups. The main hydrocarbon chain preferably does not comprise any hetero-atoms. A linear main chain is more preferred.

According to the invention, the copolymer moreover comprises side groups including carboxylic groups and polyoxyalkylate groups, and further gem-bisphosphonate groups. Advantageously, the polyoxyalkylate side groups are bound to the main chain through an ester, ether or amide bond.

Preferably, the gem-bisphosphonate groups fit the formula (IA) below:

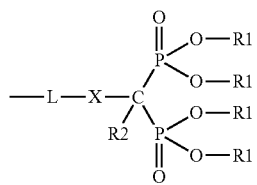

(IA)

wherein:

L represents a group for binding to the main chain, in particular a bond, an oxygen atom, a group $-NR_4-$, ($R_4$ being hydrogen or a $C_1$-$C_6$ alkyl group), or an alkylene group, preferably, L is an oxygen atom or a group $-NR_4-$;

X is a spacer group, in particular a $C_1$-$C_{20}$ alkylene group optionally substituted or a chain of groups of formula $-(QO)_n-$ in which Q represents an alkylene group with 2 to 4 carbon atoms or a mixture of alkylene groups, n being an integer varying from 1 to 500, preferably, X is a $C_1$-$C_6$ alkylene group;

R1 is, independently of each other, a monovalent group, notably a hydrogen, a $C_1$-$C_6$ alkyl group or a group of formula $-(QO)_nR_5$ wherein Q represents an alkylene group with 2 to 4 carbon atoms or a mixture of these alkylene groups, n is an integer varying from 1 to 500 and $R_5$ is a hydrogen or a $C_1$-$C_3$ alkyl, or R1 is a cation, notably an alkali metal, alkaline earth metal or ammonium cation; and R2 is a monovalent group, notably a hydrogen atom or a hydroxyl group or a $C_1$-$C_{10}$ alkyl group, preferably, R2 is a hydroxyl group.

The group L is most often bound to a carboxylic group of the copolymer and consequently the oxygen atom forms therewith an ester function and the amine groups, an amide function.

The proportion of the respective gem-bisphosphonate groups in the copolymer according to the invention may widely vary. In particular, the copolymers comprise 0.1 to 60%, in particular 1 to 40% and most particularly 2 to 10% in number of gem-bisphosphonate side groups.

The copolymer also includes as side groups, polyoxyalkylate groups. These polyoxyalkylate groups may be bound to the main chain directly or via groups formed with the present carboxylic functions, notably through an ester or amide bond.

They may also be integrated into the gem-bisphosphonate groups, notably of formula (I).

The polyoxyalkylate groups may notably be of the formula (II) below:

$$-R_e-Z-A \quad \text{(II)}$$

wherein:

$R_e$ is a $C_1$-$C_{12}$ alkylene group or a C=O group or is further absent; and Z is an oxygen atom or a group $N-R^4$, $R^4$ being hydrogen or a $C_1$-$C_6$ alkyl group; and A is a group of formula $-(QO)_n-OR^3$ wherein:

Q represents an alkylene group with 2-4 carbon atoms or a mixture of these alkylene groups;

n is an integer varying from 1 to 500; and $R^3$ represents a hydrogen atom or a $C_1$-$C_{12}$ alkyl, aryl, alkylaryl or arylalkyl group, preferably a methyl.

The copolymer generally comprises 0.001 to 80% in number, in particular, 10 to 50% in number of polyoxyalkylate groups.

According to the invention, the copolymer moreover includes carboxylic groups.

Preferably, the carboxylic groups fit the formula (III) below:

$$-C(O)-O-R_d \quad \text{(III)}$$

wherein:

$R_d$ represents H or a $C_1$-$C_{12}$ alkyl, aryl, alkylaryl or arylalkyl group or an alkali metal, alkaline earth metal or ammonium cation.

The proportion of the carboxylic groups in the copolymer may vary from 0 to 90%, in particular from 40 to 80% in number of carboxylic groups.

These carboxylic groups may be in the form of a non-dissociated acid. Most often, they will however be at least partly or totally neutralized, esterified or amidified.

The copolymer according to the invention generally has an average molar mass comprised between 1,000 and 220,000 (Mw), preferably between 10,000 and 110,000 (Mw) as determined by SEC («size exclusion chromatography») in equivalent of standard polyoxyethylene.

The polymolecularity index Ip is preferably comprised between 1 and 5, preferably between 1.5 and 3.

[Method for Preparing the Copolymers According to the Invention]

According to a second aspect, the invention proposes a method for preparing the copolymer grafted with gem-bisphosphonate groups as described below.

Several types of reaction may be suitable for preparing the copolymer according to the invention.

Notably, it may be prepared by copolymerization of suitable monomers or by modifying a polymer by grafting side groups. The latter method is also called post-grafting.

Thus, according to an embodiment, the described copolymer is prepared by bulk or solution copolymerization, in the presence of a suitable catalyst, of monomers which may polymerize bearing the sought groups respectively. It is thus possible to polymerize a mixture comprising a monomer bearing a gem-bisphosophonate group, a monomer bearing a carboxylic group and optionally a monomer bearing a polyoxyalkylate group.

A suitable monomer bearing the gem-bisphosphonate group is notably a (meth)acrylate or (meth)acrylamide bearing a gem-bisphosphonate unit, for example, obtained by reaction of a compound of formula of (I) with (meth) acryloyl chloride or (meth)acrylic anhydride.

A monomer bearing a suitable polyoxyalkylate group is notably (meth)oxypolyethylene glycol, (meth)acrylate or (meth)acrylamide.

The monomer bearing a carboxylic group may in particular be selected from unsaturated carboxylic acids such as acrylic acid, methacrylic acid, maleic acid, fumaric acid, itaconic acid and their substituted derivatives, or further a compound which may generate unsaturated carboxylic functions in situ, like maleic anhydride.

The copolymer according to the invention may then be obtained by copolymerization of these monomers, notably via a radical route under the usual conditions in the presence of a suitable initiator.

According to another embodiment, the polymer is prepared with a so-called «post-grafting» method. In this method, a polymer comprising a hydrocarbon chain and the carboxylic side groups and optionally polyalkoxylate side groups is modified by grafting gem-bisphosphonate groups.

Grafting is preferably carried out by reacting carboxylic groups with a gem-bisphosphonate compound bearing a reactive function, notably a primary or secondary amine or alcohol group.

Also, according to a second aspect, the invention is directed to a method for preparing the copolymer described above comprising the steps:
(i) polymerizing a monomer bearing a carboxylic group, optionally in the presence of a monomer bearing a polyoxyalkylate group; and
(ii) grafting the obtained polymer with a reactive gem-bisphosphonate compound.

Alternatively, it is possible to polymerize the carboxylic monomer and then esterify to the desired degree the carboxylic groups with polyoxyalkylate compounds, as this is for example described in patent application FR 2 776 285, before grafting the obtained product with a reactive gem-bisphosphonate compound.

Preferably, the reactive gem-bisphosphonate compound is a gem-bisphosphonate alcohol or amine, amines being preferred because of their better reactivity at a low temperature.

Advantageously, the reactive gem-bisphosphonate compound is of the following formula (I):

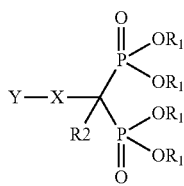

(I)

wherein:

Y is a functional group which may react with the carboxylic functions of the polymer, notably a hydroxyl, primary or secondary amine, isocyanate or thiol group;

X is a spacer group, in particular a $C_1$-$C_{20}$ alkylene group optionally substituted or a chain of groups of formula -(QO)$_n$— in which Q represents an alkylene group with 2 to 4 carbon atoms or a mixture of these alkylene groups, preferably, X is a $C_1$-$C_6$ alkylene group, n being an integer varying from 1 to 500;

R1 is, independently of each other, a monovalent group, notably a hydrogen, a cation, notably an alkali metal, alkaline earth metal or ammonium cation or a $C_1$-$C_6$ alkyl group and preferably a $C_1$-$C_3$ alkyl group; and R2 is a monovalent group, notably a hydrogen, a hydroxyl or a $C_1$-$C_{10}$ alkyl, preferably R2 is a hydroxyl group.

The polymer to be grafted will not necessarily include polyoxyalkylate groups from the moment that the gem-bisphosphonate compound includes polyoxyalkylate groups.

The grafting reaction may advantageously be conducted at a temperature above 120° C., preferably between 150 and 200° C., and in particular between 170 and 180° C. The water formed by the reaction is then removed from the reaction mixture by evaporation and the reaction product is recovered as a dry residue.

The carboxylic or phosphonic groups present in the reaction product may then be totally or partly neutralized.

[Admixture]

According to a further aspect, the invention proposes an admixture for suspensions of mineral particles, comprising the described copolymer.

In order to facilitate the application and dosage thereof, the admixture may be formulated as a solution in a suitable solvent.

Preferably, the suitable solvent comprises or consists of water. In certain cases, the use of another solvent, such as an alcohol or a glycol may be contemplated, additionally or alternatively, for example in order to facilitate solubilization.

The concentration of polymer in the admixture mainly depends on the contemplated application. Generally, the admixture comprises from 1 to 50, preferably 10 to 30% by weight of polymer based on the total weight.

Alternatively, the admixture may also appear in dry form notably as a powder.

The formulation of the admixture may moreover comprise other usual additives, such as anti-foam agents, accelerators, retardants, water-repellent agents, de-aerating agents, other dispersants, air entraining agents or stabilizers of anti-foam agents.

[Use of the Copolymers According to the Invention]

According to a fourth aspect, the invention provides the use of the admixture for fluidifying suspensions of mineral particles and for maintaining the workability of hydraulic binders.

As hydraulic binders, mention may be made in particular of cement compositions and notably concretes notably pre-fabricated concretes and ready-to-use concretes. These concretes may notably be intended for the building and civil engineering industry.

The amount of admixture to be added to the suspension of mineral particles of course depends on the sought properties and on the contemplated application. It is observed that for the preferred compositions of the invention, this dosage on the other hand varies little with the nature of the medium, and in particular, little with the chemical composition of the cements used.

Generally, for a cement composition, an admixture dosage from 0.01 to 2%, preferably from 0.05 to 1% and most particularly from 0.1 à 0.5% by weight of polymer based on the weight of the cement is suitable for most standard applications.

As an indication, an effective dosage of admixture for preparing a ready-to-use concrete composition is from 0.7 to 1.5% of a 20% dry extract weight formulation based on the weight of cement.

The action mechanism of the described polymers is not entirely understood, it being understood that that of superplasticizers in cement is still not fully elucidated in a general way.

However, it is assumed that the fluidifying effect of the superplasticizers mainly results from repulsion forces set into play between the copolymers absorbed on the surface of the grains.

The combined presence, in the copolymers with gem-bisphosphonate groups according to the invention, of long polyoxyalkylate chains having a dispersion effect and of phosphonate groups having strong capability for complexation and an exceptional absorption power towards di- or tri-valent cations such as calcium or aluminium cations, is assumed to be the reason for the particular properties as an admixture.

Moreover, it was surprisingly observed that the gem-bisphosphonate copolymers according to the invention have an excellent water reducing power/rheology maintenance compromise over a large range of concentrations of polyoxyalkylate chains.

It was further observed that the copolymers according to the invention have low sensitivity to the alkaline sulfates notably present in cement.

Indeed, the conducted tests have shown that functionalization of the PCPs by gem-bisphosphonate synthons gives the possibility of perturbing the adsorption of sulfate ions at the surface of the cement particles and therefore promoting that of the functionalized copolymer and consequently its dispersant action.

This adsorption strongly decreases in the case of high sulfate ion contents as a result of the adsorption competition on the surface of the cement grains, between sulfate ions and the copolymer. Thus, high contents of soluble sulfates generally lead to a low reduction of water, probably due to a lower initial adsorption of the copolymer. However, better workability of the compositions is observed most often, which presumably is related to better availability of the copolymer in the interstitial liquid which gives the possibility of extending the dispersant effect.

Moreover, the copolymer according to the invention advantageously has low sensitivity to the clays often present in sands and limestone fillers making up the suspensions of mineral particles.

Indeed, the presence of clays in the hydraulic compositions affects the efficiency of the superplasticizers because of their adsorption on the surface of these clays and of the insertion of their polyethoxylated grafts into the interfoliar spaces of these clays. Decrease in the maintaining of fluidity then requires an increase in the admixture dosage, which in turn generates costs and beyond which degradation of other properties may be caused, such as the compression strength and durability of the material and which may moreover lead to the occurrence of cracks.

It is assumed that this advantageous effect is related to the fact that the presence of gem-bisphosphonate groups in the copolymers according to the invention increases their affinity for the surface of the cement grains to the expense of that of the clay particles. This phenomenon may be due to the provision of additional anionic charges, related to the substitution of a carboxylate group with 4 phosphonate functions, which makes the approach towards the clays more difficult and therefore the adsorption at their surface.

The obtained grafted copolymers as described above are of particular interest as plasticizers for suspensions of mineral particles, notably of cement compositions and plaster formulations.

Indeed, they have:

high water reducing power, insensitivity to the alkaline sulfates of the cements, decrease in the sensitivity to clays present in the sands, very good fluidifying power of hydraulic compositions with very good retention of fluidity.

[Compositions of Mineral Particles]

Finally, according to a last aspect, the invention is directed to a composition of mineral particles comprising the copolymer according to the invention.

The compositions thus with an admixture have prolonged workability with low dosage, including in the presence of high contents of alkaline sulfates and/or clays. Consequently they are of interest for a wide range of applications, in particular ready-to-use concretes, self-compacting concretes, high or ultra high performance concretes (HPC or UHPC) or precast concrete.

The invention will be better explained with reference to the examples which follow, given as non-limiting examples.

EXAMPLES

A. Preparation of the Bis-Phosphonate Synthon

Example 1

Preparation of 1-hydroxyethylene-1,1-bisphosphonic acid (HEDP)

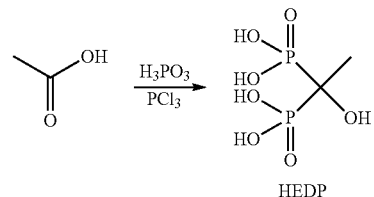

HEDP

In a 1,000 mL three-neck flask, provided with magnetic stirring, surmounted with a condenser and with nitrogen inertization and placed in a thermostated oil bath and connected to a vacuum pump, 60 g (1 mole) of acetic acid, 123 g (1.5 moles) of phosphorous acid and 500 mL of anhydrous chlorobenzene are loaded. The mixture is brought to a temperature of 100° C. with stirring. The formation of a homogenous solution is observed. 206 g (1.5 moles) of phosphorus trichloride (PCl$_3$) are then slowly added into the medium. The reaction mixture is maintained at 100° C. for a further three hours and then left to cool at room temperature. The solid residue obtained is washed with chlorobenzene and then dissolved in 500 mL of water and brought to boiling with reflux for 1 hour. After cooling, the solution is treated with active carbon and then filtered. The raw acid precipitates by adding an excess of hot methanol and after separation, the product is recrystallized from one liter of water at 100° C.

The yield is 87% of 1-hydroxy ethylene-1,1-bisphosphonic acid. The reaction product is characterized with $^{31}$P NMR (CDCl$_3$), $^1$H NMR (CDCl$_3$) and $^{13}$C NMR.

Example 2

Preparation of 1-hydroxy-3-amino-propylene-1,1-bisphosphonic acid (AHP)

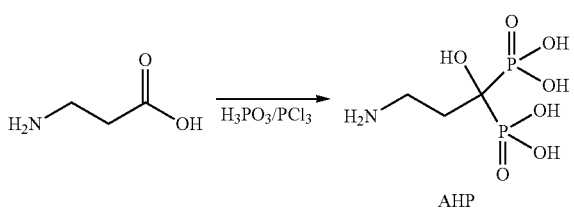 [SMILES: NCCC(=O)O ; NCCC(O)(P(=O)(O)O)P(=O)(O)O]

AHP

In a 1,000 mL three-neck flask provided with magnetic stirring, surmounted with a condenser and with nitrogen inertization and placed in a thermostated oil bath and connected to a vacuum pump, 91 g (1 mole) of 3-amino-propionic acid, 123 g (1.5 moles) of phosphorous acid and 500 mL of anhydrous chlorobenzene are added. The mixture is brought to a temperature of 100° C. with stirring. The formation of a homogeneous solution is observed. 206 g (1.5 moles) of phosphorus trichloride ($PCl_3$) are then slowly introduced into the medium. The reaction mixture is maintained at 100° C. for a further three hours and then left to cool at room temperature. The obtained solid residue is washed with chlorobenzene and then dissolved in 500 mL of water and brought to boiling with reflux for 1 hour. After cooling, the solution is treated with active carbon and then filtered. The raw acid precipitates by addition of an excess of hot methanol and after separation, the product is recrystallized from one liter of water at 100° C.

The yield is 82% of 1-hydroxy-3-amino-propylene-1,1-bisphosphonic acid. The reaction product was characterized with $^{31}P$ NMR ($CDCl_3$), $^1H$ NMR ($CDCl_3$) and $^{13}C$ NMR.

Example 3

Preparation of 1-hydroxy-4-amino-butylene-1,1-bisphosphonic acid (BHP)

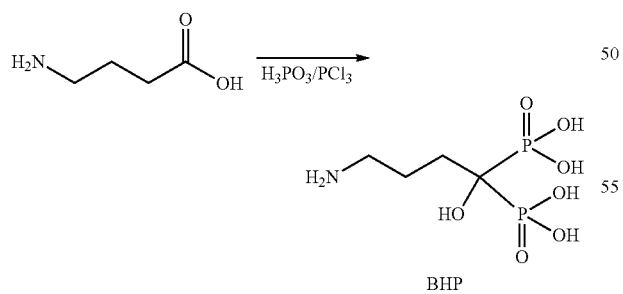

BHP

In a 1,000 mL three-neck flask provided with magnetic stirring, surmounted with a condenser and with nitrogen inertization and placed in a thermostated oil bath and connected to a vacuum pump, 105 g (1 mole) of 4-aminobutyric acid, 123 g (1.5 moles) of phosphorous acid and 500 mL of anhydrous chlorobenzene are loaded. The mixture is brought to a temperature of 100° C. with stirring. The formation of a homogeneous solution is observed. 206 g (1.5 moles) of phosphorus trichloride ($PCl_3$) is then slowly introduced into the medium. The reaction mixture is maintained at 100° C. for a further three hours and then left to cool at room temperature. The obtained solid residue is washed with chlorobenzene and then dissolved in 500 mL of water and brought to boiling with reflux for 1 hour. After cooling, the solution is treated with active carbon and then filtered. The raw acid precipitates by addition of an excess of hot methanol and after separation, the product is recrystallized from a liter of water at 100° C.

The yield is 77% of 1-hydroxy-4-amino-butylene-1,1-bisphosphonic acid. The reaction product was characterized by $^{31}P$ NMR ($CDCl_3$), $^1H$ NMR ($CDCl_3$) and $^{13}C$ NMR.

B. Modification of a Polymer by Crafting the Gem-Bisphosphonate Synthon

After obtaining a non-functionalized reference phosphorus-containing copolymer (Example 4), tests for grafting the phosphonate synthon conducted with HEDP are presented in order to determine the best operating conditions (examples 5A-5C). These grafting conditions were then used for grafting HEDP, AHP and BHP synthons at different levels (Examples 6A-6C, 7A-7C et 8A-8C).

Example 4

Preparation of a Reference Polyalkoxylated Polycarboxylic Copolymer

In a 500 mL two-neck flask provided with magnetic stirring, surmounted with a condenser and with nitrogen inertization and placed in a thermostated oil bath, 73.57 g (323.4 mmoles) of polymethacrylic acid (TP 941, marketed by COATEX, acid index 181.1 mg KOH/g) are loaded and then 0.48 g (5.95 mmoles) of soda (aqueous solution with 50% by weight of NaOH) are introduced. One then proceeds with loading 34.35 g (46 mmoles) of methoxypolyethyleneglycol (MPEG) with a molar mass of 750 g/mol and then with 91.60 g (46 mmoles) of methoxypolyethyleneglycol (MPEG) with molar mass 2,000 g/mol and the temperature of the reaction medium is brought to 175° C. When the temperature of the reaction medium attains 100° C., the reactor is put under partial vacuum (<20 mbars).

The moment when the reaction medium becomes homogeneous is taken as T0, the time of the beginning of the reaction. The esterification reaction is left to continue for 7 hours at 175° C. before allowing the reaction medium to return to room temperature.

An anhydrous base is obtained having a comb copolymer mass of 147.5 g i.e. 73.8% based on the initial reaction mixture.

Examples 5A-5C

Optimization of the Grafting Conditions of the Phosphonate Synthon

In order to evaluate the effect of the reaction conditions on the grafting of the polycarboxylic acid, Example 4 was repeated by varying the moment when the gem-bisphosphonate reagent HEDP is introduced, as prepared in the previous examples.

In Example 4, the reaction is conducted without adding any gem-bisphosphonate synthon so as to be used as a reference. In the Examples 5A, the gem-bisphosphonate synthon (HEDP) is added at the beginning of the reaction, when the reaction medium becomes homogeneous (T0) and 4 hours after this moment, respectively.

The reaction mixtures from these reactions are analyzed in terms of acid index and of residual MPEG content by GPC according to the following procedure.

In a first phase, MPEG standards with increasing concentrations are injected and then the corresponding areas are determined. Measurement of the area of the MPEG peak of the sample to be analyzed gives the possibility of accessing the residual MPEG level. The injections are accomplished at 40° C., the columns used are Aquagel Guard OH 8 μm (marketed by Agilent Technologies) positioned in series with two Aquagel OH30 columns (also marketed by Agilent Technologies).

TABLE 1

Conditions of the reaction according to Examples 5A-5C

| EXAMPLE | Reaction mixture | HEDP Amount [molar %] | Introduced | Acid index IA | Residual Polyox. |
|---|---|---|---|---|---|
| 4 (EPB 662054) | Methacrylic acid MPEG | — | N/A | 20.384 | 3.87% |
| 5A (EPB 662055) | Methacrylic acid MPEG | 4 | At the start | 36.741 | 29.84% |
| 5B (EPB 662056) | Methacrylic acid MPEG | 4 | At T0 | 33.424 | 27.88% |
| 5C (EPB 662058) | Methacrylic acid MPEG | 4 | At T0 + 4 h | 33.769 | 3.83% |

The results are summarized in the table 1 above

It is seen that the simultaneous introduction of the gem-bisphosphonate synthon with the polyalkoxylated compounds perturbs the esterification reaction.

Deferred introduction into the reaction medium on the other hand, for example after 4 hours of reaction, gives the possibility of again finding an MPEG grafting level equivalent to that of the reference reaction without any phosphonate synthon.

These operating conditions are the ones which were retained for the subsequent study.

Example 6A-6C

Preparation of Copolymers of the PCP Type Crafted with HEDP

In a 500 mL two-neck flask provided with magnetic stirring, surmounted with a condenser and with nitrogen inertization and placed in a thermostated oil bath, 73.57 g (323.4 mmoles) of polymethacrylic acid (TP 941, marketed by COATEX, acid index 181.1 mg KOH/g) are loaded and 0.48 g (5.95 mmoles) of soda (aqueous solution with 50% by weight of NaOH) are then introduced. It is then proceeded with the loading of 34.35 g (46 mmoles) of methoxypolyethyleneglycol (MPEG) with a molar mass of 750 g/mol and then with 91.60 g (46 mmoles) of methoxypolyethyleneglycol (MPEG) with a molar mass of 2,000 g/mol and the temperature of a reaction medium is brought to 175° C. When the temperature of the reaction medium attains 100° C., the reactor is set under partial vacuum (<20 mbars).

The moment when the reaction medium becomes homogeneous is taken as T0, the time of the beginning of the reaction. After 4 hours of baking at 175° C., 4.11 g of bisphosphonate synthon according to Example 1 are introduced very slowly and the esterification reaction is left to further continue for 3 hours at 175° C. before allowing the reaction medium to return to room temperature.

An anhydrous base is obtained having a mass of grafted copolymer of 143.3 g i.e. 71.7% based on the initial reaction mixture.

The obtained solution of copolymer bearing carboxylic functions, polyether grafts and gem-bisphosphonic units, is then formulated by adding 0.5% by weight of oleic amine with 2 moles of ethylene oxide (marketed under the name of NORAMOX $O_2$ by CECA) and 1.2% by weight of tributylphosphate (antifoam agent).

Finally, the product is diluted with water in order to obtain a 20% dry extract and it is neutralized with sodium hydroxide at pH 7.

The thereby prepared dispersant is ready to use.

Example 7A-C

Preparation of Copolymers of the PCP Type Crafted with AHP

Example 6 is repeated but however replacing the gem-bisphosphonic synthon HEDP with the amount of gem-bisphosphonic synthon AHP prepared in Example 2 indicated in Table 2 below.

An anhydrous base is obtained having a mass of grafted copolymer of 144.5 g i.e. 72.6% based on the initial reaction mixture.

The obtained solution of copolymer bearing carboxylic functions, polyether grafts and gem-bisphosphonic units, is then formulated by adding 0.5% by weight of oleic amine with 2 moles of ethylene oxide (marketed under the name of NORAMOX $O_2$ by CECA) and 1.2% by weight of tributylphosphate (anti foam agent).

Finally, the product is diluted with water in order to obtain a 20% dry extract and it is neutralized with sodium hydroxide at pH 7.

The thereby prepared dispersant is ready to use.

TABLE 2

Reagents for preparing the copolymers of Examples 6-9

| | | Gem-bisphosphonic synthon | | |
|---|---|---|---|---|
| EX. | PCP type copolymer | Type | Proportion [molar %] | Mass [g] |
| 6A | EPB 762.013 | HEDP | 2 | 145.5 |
| 6B | EPB 762.014 | HEDP | 4 | 143.3 |
| 6C | EPB 762.015 | HEDP | 6 | 141.1 |
| 7A | EPB 762.022 | AHP | 2 | 146.1 |
| 7B | EPB 762.023 | AHP | 4 | 144.5 |
| 7C | EPB 762.024 | AHP | 6 | 142.9 |
| 8A | EPB 762.034 | BHP | 2 | 146.1 |
| 8B | EPB 762.035 | BHP | 4 | 144.6 |
| 8C | EPB 762.036 | BHP | 6 | 142.9 |
| 9A | EPB 762.013 + EPB 709028 | HEDP | 2 | ND |
| 9B | EPB 762.014 + + EPB 709028 | HEDP | 4 | ND |
| 9C | EPB 762.015 + + EPB 709028 | HEDP | 6 | ND |

Example 8A-C

Preparation of Copolymers of the PCP Type Crafted with BHP

Example 6 is repeated but however by replacing the gem-bisphosphonic synthon HEDP with the amount of gem-bisphosphonic synthon BHP prepared in Example 3 as indicated in Table 2 above.

An anhydrous base is obtained having a mass of grafted copolymer of 144.6 g i.e. 72.73% based on the initial reaction mixture.

The obtained solution of copolymer bearing carboxylic functions, polyether grafts and gem-bisphosphonic units, is then formulated by adding 0.5% by weight of oleic amine with 2 moles of ethylene oxide (marketed under the name of NORAMOX $O_2$ by CECA) and 1.2% by weight of tributylphosphate (anti foam agent).

Finally, the product is diluted with water in order to obtain a 20% dry extract and it is neutralized with sodium hydroxide at pH 7.

The thereby prepared dispersant is ready for use.

Example 9A-C

Preparation of Copolymers of the PCP Type Crafted with HEDP

Example 6 is repeated but however by adding in the final copolymer a proportion of copolymer of the EPB 729.028 type obtained under the operating conditions of Example 4 but only containing carboxylic functions and methoxypolyethyleneglycol with a molar mass of 2,000 g/mol.

The obtained solution of the mixture of copolymers bearing carboxylic functions, polyether grafts and gem-bisphosphonic units, is then formulated by adding 0.5% by weight of oleic amine with 2 moles of ethylene oxide (marketed under the name of NORAMOX $O_2$ by CECA) and 1.2% by weight of tributylphosphate (anti foam agent).

Finally, the product is diluted with water in order to obtain a 20% dry extract and it is neutralized with sodium hydroxide at pH 7.

The thereby prepared dispersant is ready for use.

C. Evaluation of the Application Properties

1. Water Reducing Power

In order to evaluate the water reducing power of the copolymers according to the invention, mortars were formulated by adding the prepared copolymers to Examples 6 to 9 as a plasticizer.

The composition of the prepared mortar is detailed in Table 3 below. The non-grafted copolymer (Example 4 EPB 662054 and the mixture EPB 762.014+EPB 729.028, respectively) is used as a reference (REF).

The mortar is prepared according to the following procedure:

Two standardized FULCHIRON sands are introduced into the bowl of a PERRIER kneader. After kneading the sands for 30 seconds at a rate of about 140 rpm, the pre-wetting water which represents ⅓ of the total water to be introduced is added within 15 seconds. The mixing is continued for 15 seconds before leaving the mass at rest for 4 minutes. Next, the cement and the limestone filler (origin: ERBRAY provided by MEAC) are introduced and the mixing is then continued for 1 minute before adding the remainder of the mixing water as well as the totality of the admixture within 30 seconds. The kneader is then stopped for a few instants in order to scrape the edges of the kneading bowl to have a proper homogenous mass and mixing is then continued for again 1 minute at a fast rate of 280 rpm.

TABLE 3

Composition of the mortar used for evaluating workability

| Component | Mass [g] |
| --- | --- |
| CEM I (Le Havre cement 01/10) | 624.9 |
| ERBLAY filler | 412.1 |
| AFNOR sand | 1350 |
| FULCHIRON sand | 587.7 |
| Total water | 375.1 |

The workability of the mortars formulated with the copolymers according to the invention was evaluated by measuring the spread diameter (slump flow) according to the procedure described hereafter.

A mold of frustoconical shape without any bottom reproducing the Abrams cone (see standard NF 18-451, 1981) at a scale of 0.5 is filled; in order to carry out spreading, the cone is lifted perpendicularly to the plate by completing a quarter turn. The spreading is measured at 5, 30, 60 and 90 minutes along 2 diameters at 90° with a tape measure. The result of the spreading measurement is the average of the 2 values to within +/−1 mm. The tests were carried out at 20° C.

The dosage of the grafted copolymer is determined so as to attain a target spread comprised between 310 and 330 mm. Unless indicated otherwise, the dosage is expressed in percent by weight based on the total weight of the binder (filler+cement).

The results obtained for the mortars formulated with the copolymers grafted with HEDP of Example 6 are transferred into Table 4 below.

Upon examining the results, it is seen that the grafting with 2 or 4% of HEDP gives the possibility of substantially lowering the dosage (passing from 0.60% to 0.35%) for an equivalent initial spread.

TABLE 4

Spreading of a mortar with an admixture of copolymers of Example 6

| EX. | Grafting [molar %] | Dosage [%] | Spreading T [mins] | | | | | Loss of fluidity [%] |
| --- | --- | --- | --- | --- | --- | --- | --- | --- |
| | | | 5 | 30 | 60 | 90 | 120 | |
| REF | — | 0.5 | 335 | 325 | 300 | 280 | 245 | 26.87 |
| REF | 4% HEDP without grafting | 0.5 | 315 | 310 | 290 | 270 | 245 | 22.22 |
| 6A | 2% HEDP | 0.35 | 320 | 245 | 190 | 165 | 125 | 60.94 |
| 6B | 4% HEDP | 0.35 | 340 | 275 | 220 | 195 | 155 | 54.41 |
| 6C | 6% HEDP | 0.35 | 340 | 225 | 195 | 155 | 125 | 63.24 |

It is moreover verified that by simply adding to the control formulation, 4% of HEDP, (EPB 760.020), which is then not grafted to the copolymer, it is not possible to modify the water reducing power of the control grafted copolymer.

Improvement in the water reducing power of the bisphosphonic grafted copolymers may be explained by a larger affinity for the surface of the cement grains.

The results obtained for the mortars formulated with the AHP-grafted copolymers prepared in Example 7 as described earlier are transferred into Table 5 below.

TABLE 5

Spreading of a mortar with admixture of copolymers of Example 7

| EX. | Grafting [molar %] | Dosage [%] | Spreading T [mins] | | | | | Loss of fluidity [%] |
|---|---|---|---|---|---|---|---|---|
| | | | 5 | 30 | 60 | 90 | 120 | |
| REF | — | 0.5 | 335 | 335 | 290 | 270 | 245 | 26.87 |
| REF | — | 0.5 | 340 | 340 | 320 | 310 | 280 | 17.65 |
| 7A | 2% AHP | 0.35 | 335 | 245 | 215 | 170 | 155 | 53.73 |
| 7B | 4% AHP | 0.35 | 320 | 225 | 175 | 140 | 120 | 62.50 |
| 7C | 6% AHP | 0.35 | 340 | 235 | 200 | 170 | 140 | 58.82 |

It is seen that by grafting 2, 4 or 6% of AHP, it is also possible to lower the dosage of superplasticizer (passing from 0.50% to 0.35%) for an equivalent initial spread.

The results obtained for the mortars formulated with the BHP-grafted copolymers prepared in Example 8 as described earlier are transferred into Table 6 below.

TABLE 6

Spreading of a mortar with an admixture of copolymers of example 8

| EX. | Grafting [molar %] | Dosage [%] | Spreading T [mins] | | | | | Loss of fluidity [%] |
|---|---|---|---|---|---|---|---|---|
| | | | 5 | 30 | 60 | 90 | 120 | |
| REF | — | 0.5 | 330 | 330 | 315 | 260 | 245 | 25.76 |
| REF | — | 0.4 | 330 | 330 | 270 | 225 | 175 | 46.97 |
| 8A | 2% BHP | 0.4 | 330 | 270 | 245 | 190 | 160 | 51.52 |
| 8B | 4% BHP | 0.4 | 340 | 290 | 265 | 200 | 165 | 51.47 |
| 8C | 6% BHP | 0.35 | 320 | 200 | 160 | 125 | 120 | 62.50 |

The obtained results show that the grafting of 2 or 4% of BHP also allows lowering of the dosage (passing from 0.5% to 0.4%) for an equivalent initial spread.

With the results presented above, it is possible to conclude that the introduction of bis-phosphonic units on a PCP backbone modifies the water reducing power of the copolymers.

Without intending to be bound by any theory, this observation may be explained by increased affinity of the grafted copolymers for the surface of the cement particles.

2. Improvement in the Water Reducing Power while Maintaining Fluidity

Moreover, it was surprisingly observed that these polymers with gem-bisphosphonate groups give the possibility of significantly improving the water reducing power without degrading the maintenance of rheology on a wide range of concentrations of polyoxyalkylene chains in the copolymer, expressed by the ester level in Table 8.

TABLE 7

Composition of the mortar used for evaluating workability

| Mortar composition | Batch | Mixed [g] |
|---|---|---|
| CEM I 52, 5 R SPLC | 19 May 2010 | 800 |
| DURCAL 10 filler | ND | 120 |
| AFNOR sand | ND | 1350 |
| Total water | ND | 300 |

TABLE 8

Spreading of a mortar with an admixture of copolymers of Example 9

| SPLC 52, 5 R | Commercial dosage [&] | Dry dosage [%] | Spread [mm] | | | MPEG 2000 level | HEDP level | Overall ester level |
|---|---|---|---|---|---|---|---|---|
| | | | 5 | 3 | 60 | | | |
| EPB 819019 | 1.20 | 0.30 | 315 | 315 | 310 | 25 | 0 | 25 |
| EPB 819012 | 1.00 | 0.25 | 310 | 320 | 310 | 25 | 4 | 29 |
| EPB 819027 | 0.85 | 0.21 | 300 | 295 | 295 | 25 | 8 | 33 |
| EPB 819035 | 0.50 | 0.13 | 305 | 275 | 290 | 25 | 12 | 37 |
| EPB 819036 | 0.50 | 0.13 | 290 | 275 | 285 | 25 | 16 | 41 |

It is seen upon examining Table 8 above that by using an additive including a polyalkoxylated polycarboxylic copolymer grafted with 4% and 8% of HEDP in a cement formulation it is possible to reduce the dosage of superplasticizer with maintaining fluidity over time.

2. Sensitivity to Alkaline Sulfates

In order to evaluate the impact of the presence of alkaline sulfates on the efficiency of the copolymers according to the invention as a superplasticizer, one proceeded with tests with mortars having variable sulfate content.

The content of alkaline sulfates in the mortars was modified by adding powdered potassium sulfate to the cement (0.3 and 0.6% by weight based on the dry/dry weight of the cement). The mortar was then prepared according to the formulation indicated in Table 9 below, by adding to the mixing water, the indicated dosage of reference copolymer.

The spread of these mortars was evaluated as described above.

TABLE 9

Composition of the mortar used for evaluating the sensitivity to sulfates

| Component | Mass [g] |
|---|---|
| CEM I (Le Havre cement 01/10) | 624.9 |
| ERBLAY filler | 412.1 |
| AFNOR sand | 1350 |
| FULCHIRON sand | 587.7 |
| Total water | 375.1 |

The obtained results are transferred into Tables 10 and 11 below, respectively. The indicated total sulfate concentration takes into account the level of alkaline compounds initially present in Le Havre cement (LH), evaluated to be 0.25% by weight (dry/dry basis).

It is observed that the referenced superplasticizer dosage required for obtaining a targeted spread is nearly trebled in the presence of an additional 0.6% by weight of alkaline sulfate.

TABLE 10

Effect of the sulfates - reference superplasticizer

| EX. | Grafting [molar %] | Added K₂SO₄ [% by weight of the cement] | Total alkaline sulfates [% by weight] | Dosage [%] | Spread T [mins] | | | | |
|---|---|---|---|---|---|---|---|---|---|
| | | | | | 5 | 30 | 60 | 90 | 120 |
| REF | — | — | 0.25 | 0.5 | 320 | 295 | 240 | 180 | 140 |
| REF | — | 0.3 | 0.55 | 0.8 | 310 | 305 | 270 | 230 | 200 |
| REF | — | 0.6 | 0.85 | 1.3 | 325 | 320 | 315 | 300 | 280 |

The tests were then repeated by using the copolymer of Example 6B (grafted with 4% of HEDP) in the mortar formulation. The obtained results are summarized in Table 11 below.

TABLE 11

Effect of the sulfates - copolymer of Example 6, constant spread

| EX. | Grafting [molar %] | Added K₂SO₄ [% by weight] | Dosage [%] | Spread T [mins] | | | | |
|---|---|---|---|---|---|---|---|---|
| | | | | 5 | 30 | 60 | 90 | 120 |
| REF | — | — | 0.5 | 320 | 295 | 240 | 180 | 140 |
| REF | — | 0.3 | 0.8 | 310 | 305 | 270 | 230 | 200 |
| REF | — | 0.6 | 1.3 | 325 | 320 | 315 | 300 | 280 |
| 6B | 4% (HEDP) | — | 0.35 | 310 | 200 | 150 | 110 | 110 |
| 6B | 4% (HEDP) | 0.3 | 0.5 | 340 | 325 | 290 | 260 | 215 |
| 6B | 4% (HEDP) | 0.6 | 0.5 | 265 | 230 | 200 | 170 | 150 |

These results demonstrate the interesting effect of the copolymers according to the invention at the level of sensitivity to the presence of alkaline sulfates. Indeed, it is seen that the copolymer according to the invention tolerates much higher alkaline sulfate levels in the cement as compared with the reference plasticizer.

In order to better evaluate the insensitivity to the sulfate ions brought by the bisphosphonic functionalization, the previous tests were repeated, with the same mortar composition, by adding and increasing concentration of potassium sulfate but by imposing constant dosage.

The results obtained for the copolymers of Example 6A and 6B are collected in Table 12 below.

The results demonstrate that functionalization with 4% of HEDP gives the possibility of suppressing the detrimental effect of 0.4% by weight of alkaline sulfate in the cement under the conditions of the test.

Moreover, it is seen that a copolymer grafted with 2% of HEDP in a cement mortar loaded with 0.3% by weight of potassium sulfate has a similar behavior or even a slightly superior behavior in maintaining rheology as that of the reference. In other words, grafting of the reference copolymer with 2% of HEDP gives the possibility of suppressing the detrimental effect of 0.3% by weight of potassium sulfate presence in a cement.

TABLE 12

Effect of the sulfates - copolymers of Example 6, constant dosage

| EX. | Grafting [molar %] | Added K₂SO₄ [% by weight] | Dosage [%] | Spread T [mins] | | | | |
|---|---|---|---|---|---|---|---|---|
| | | | | 5 | 30 | 60 | 90 | 120 |
| REF | — | — | 0.5 | 310 | 275 | 220 | 170 | 145 |
| 6A | 2% (HEDP) | — | 0.4 | 340 | 280 | 200 | 155 | 120 |
| 6A | 2% (HEDP) | 0.3 | 0.5 | 320 | 310 | 280 | 230 | 180 |
| 6A | 2% (HEDP) | 0.6 | 0.5 | 225 | 185 | 160 | 140 | 120 |
| REF | — | — | 0.5 | 320 | 300 | 255 | 200 | 160 |
| 6B | 4% (HEDP) | 0.3 | 0.5 | 340 | 325 | 290 | 260 | 215 |
| 6B | 4% (HEDP) | 0.4 | 0.5 | 320 | 300 | 255 | 210 | 175 |
| 6B | 4% (HEDP) | 0.5 | 0.5 | 295 | 270 | 215 | 185 | 160 |
| 6B | 4% (HEDP) | 0.6 | 0.5 | 265 | 230 | 200 | 170 | 150 |

The use of the copolymers according to the invention as a superplasticizer is therefore less sensitive towards alkaline sulfates in the cements, as compared with the non-grafted copolymer. This observation may be explained by a complexing power of the phosphorate group towards calcium ions which is greater as compared with sulfate ions.

3. Sensitivity to Clays

Superplasticizers are also sensitive to the presence of clays in the compositions, generally in the sands.

In order to evaluate this sensitivity of the copolymers according to the invention, the spreading of mortars formulated with sand polluted with a clay (montmorillonite KSF) was measured and compared with that of a mortar formulated with a clean non-polluted sand.

Unless indicated otherwise, the clay percentage is expressed in percent by dry weight based on the total dry sand, consisting of AFNOR sand and of FULCHIRON sand, the added clay is introduced with the sand before adding pre-wetting water.

The mortars were prepared according to the formulation indicated in Table 7 above, by using the cement with a strong level of alkaline compounds (CEM I 52.5 N cement from Saint Pierre la Cour, marketed by Lafarge) and the copolymer according to Example 9B (mixture of EPB 762.014 grafted with 4% HEDP and of EPB 729.028).

The results of the tests are shown in Table 13 below.

These results show that the studied copolymers according to invention are significantly less sensitive to clay present in the sands, to the extent of widely neutralizing the detrimental effect of 1% by weight of clay (based on dry sand) on the fluidity of the cement composition.

TABLE 13

Clay effect - copolymer of example 9

| EX. | Grafting [molar %] | Added clay * [% by weight] | Dosage | Spread T [mins] | | | | |
|---|---|---|---|---|---|---|---|---|
| | | | | 5 | 30 | 60 | 90 | 120 |
| REF | — | — | 1.0 | 315 | 295 | 290 | 285 | 280 |
| REF | — | 1 | 1.0 | 180 | 160 | 145 | 120 | 110 |
| REF | — | 1 | 1.2 | 215 | 180 | 170 | 160 | 150 |
| 9B | 4% (HEDP) | 1 | 1.0 | 275 | 250 | 240 | 225 | 210 |
| 9B | 4% (HEDP) | 1 | 1.2 | 335 | 320 | 300 | 295 | 285 |

* The added clay is KSF montmorillonite marketed by ALDRICH

4. Efficiency on Composite Cements

In order to evaluate the robustness of the copolymers according to the invention, the superplasticising effect was studied on composite cements with different composition.

More specifically, a cement was tested, including as a substitution binder, flying ashes (CEM II/A-V cement (Saint Pierre La Cour, marketed by LAFARGE)). The mortars were prepared according to the formulation given in Table 9 and added with admixture with various dosages of copolymer of Example 9B.

The spreading values obtained for these mortars are collected in Table 14 below.

TABLE 14

Effect on flying ash cement

| EX. | Grafting [molar %] | Dosage [%] | Spread T [mins] | | | | |
|---|---|---|---|---|---|---|---|
| | | | 5 | 30 | 60 | 90 | 120 |
| REF | — | 1.0 | 325 | 315 | 310 | 300 | 260 |
| 9B | 4% (HEDP) | 1.0 | 360 | 370 | 380 | 380 | 370 |
| 9B | 4% (HEDP) | 0.8 | 320 | 340 | 345 | 340 | 320 |

The obtained results show that in the presence of flying ashes, the copolymers according to the invention have a higher water reducing power than the reference superplasticizer.

Moreover, it is noted that by reducing the dosage by 20% of the copolymer according to the invention it is possible to obtain a cement composition having a rheological behavior in terms of maintaining fluidity, superior to that of the reference superplasticizer.

On the other hand, a cement including as a substitution binder a slag (CEM III/A 42.5 N-LH PM-ES-CP1 (marketed by Lafarge) of the following composition, was tested:

Clinker 35% by weight (C3A 8.6%-C3S 60%-C4AF 11)

Slag 62% by weight

Secondary constituents 3% by weight

Gypsum 4.8% by weight.

The mortars were prepared according to the formulation given in Table 9 and added with admixture with different dosages of copolymer of Example 9B.

The spread values obtained for these mortars are collected in Table 15 below.

TABLE 15

Effect on slag cement

| EX. | Grafting [molar %] | Dosage [%] | Spread T [mins] | | | | |
|---|---|---|---|---|---|---|---|
| | | | 5 | 30 | 60 | 90 | 120 |
| REF | — | 0.5 | 325 | 345 | 330 | 300 | 280 |
| 9B | 4% (HEDP) | 0.5 | 380 | 390 | 380 | 330 | 310 |
| 9B | 4% (HEDP) | 0.4 | 325 | 320 | 260 | 225 | 190 |

The obtained results show that in the presence of slag as a substitution binder, the copolymers according to the invention have a higher water reducing power than the reference superplasticizer.

The experimental data above confirm the benefit of the copolymers according to the invention as a superplasticizer for compositions of hydraulic binders. These copolymers actually have a higher water reducing power, low sensitivity to alkaline sulfates and to clays as well as high robustness and good maintenance of rheology in a wide range of ester levels.

The invention claimed is:

1. A method of maintaining workability of hydraulic binders comprising adding to said hydraulic binders an admixture comprising a copolymer comprising a main hydrocarbon chain and side groups, wherein the side groups comprise carboxylic groups, polyoxyalkylate groups and gem-bisphosphonate groups, wherein the copolymer has an average molar mass between 10,000 and 110,000 (Mw) as determined by size exclusion chromatography in equivalent of standard polyoxyethylene, wherein:

the carboxylic groups of the copolymer fit the formula (III) below:

$$-C(O)-O-R_d \quad \text{(III)}$$

wherein:

$R_d$ represents H or a $C_1$-$C_{12}$ alkyl, aryl, alkylaryl or arylalkyl group or an alkali metal, alkaline earth metal or ammonium cation; and the gem-bisphosphonate side groups:

fit the formula (IA) below:

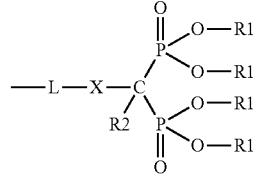

(IA)

wherein:

L represents a group —$NR_4$— for binding to a carboxylic group of the main chain wherein $R_4$ is a hydrogen or a $C_1$-$C_6$ alkyl group;

X is a $C_1$-$C_{20}$ alkylene spacer group, optionally substituted;

R1 are, independently of each other, H; or a cation; and

R2 is a hydrogen atom, a hydroxyl group or a $C_1$-$C_{10}$ alkyl group; or is a result of a grafting with 1-hydroxyethylene-1,1-bisphosphonic acid (HEDP) to carboxylic group of the main chain.

2. The method according to claim 1, wherein the polyoxyalkylate side groups of the copolymer are bound to the main chain through an ester, ether or amide bond.

3. The method according to claim 1, wherein the gem bisphosphonate groups of the copolymer is a result of a grafting with a compound selected from the group consisting of 1-hydroxy-3-amino-propylene-1,1-bisphosphonic acid (AHP) and 1-hydroxy-4-amino-butylene-1,1-bisphosphonic acid (BHP) to carboxylic group of the main chain.

4. The method according to claim 1, wherein the polyoxyalkylate groups of the copolymer are of the formula (II) below:

$$—R_e—Z-A \quad (II)$$

wherein:

$R_e$ is a $C_1$-$C_{12}$ alkylene group, a C=O group or is absent; and

Z is an oxygen atom or a group N—$R^4$, wherein $R^4$ is a hydrogen or a $C_1$-$C_6$ alkyl group; and A is a group of formula $(QO)n$-$R^3$ wherein:
Q represents an alkylene group with 2 to 4 carbon atoms or a mixture of these alkylene groups;
n is an integer varying from 1 to 500; and
$R^3$ represents a hydrogen atom or a $C_1$-$C_{12}$ alkyl, aryl, alkylaryl or arylalkyl group.

5. The method according to claim 1, wherein the carboxylic groups of the copolymer fit the formula (III) below:

$$—C(O)—O—R_d \quad (III)$$

wherein:
$R_d$ represents H.

6. The method according to claim 1, wherein admixture is in a solvent comprising 1 to 50% by weight of copolymer based on the total weight of the admixture.

7. The method according to claim 1, wherein the copolymer comprises from 2 to 10% in number of gem-bisphosphonate side groups.

8. The method according to claim 1, wherein the gem-bisphosphonate groups of the copolymer are of formula (IA), X being a $C_1$-$C_6$ alkylene group.

9. The method according to claim 1, wherein the gem bisphosphonate groups of the copolymer are of formula (IA), $R_1$ being a hydrogen atom or an alkali metal, earth alkaline metal or ammonium cation.

10. The method according to claim 1, wherein the gem bisphosphonate groups are of formula (IA), $R^2$ being a hydroxyl group.

11. The method according to claim 1, wherein in the bisphophonate group of formula (IA), R1 is a hydrogen.

12. The method according to claim 1, wherein in the bisphophonate group of formula (IA), R1 is an alkali metal, an alkaline earth metal, or an ammonium cation.

13. The method according to claim 4, wherein, in the polyoxyalkylate groups of the copolymer of formula (II), A is a group of formula $(QO)n$-$R^3$ wherein $R^3$ is a methyl.

14. The method according to claim 6, wherein the solution comprises 10 to 30% by weight of copolymer based on the total weight of the admixture.

* * * * *